US012220521B2

(12) United States Patent
Säll (10) Patent No.: US 12,220,521 B2
(45) Date of Patent: Feb. 11, 2025

(54) TENSIONING ARRANGEMENT FOR AEROSOL DISPENSER AND AEROSOL DISPENSER

(71) Applicant: SHL MEDICAL AG, Zug (CH)

(72) Inventor: Daniel Säll, Segeltorp (SE)

(73) Assignee: SHL Medical AG, Zug (CH)

( * ) Notice: Subject to any disclaimer, the term of this patent is extended or adjusted under 35 U.S.C. 154(b) by 950 days.

(21) Appl. No.: 17/275,119

(22) PCT Filed: Sep. 12, 2019

(86) PCT No.: PCT/EP2019/074313
§ 371 (c)(1),
(2) Date: Mar. 10, 2021

(87) PCT Pub. No.: WO2020/064341
PCT Pub. Date: Apr. 2, 2020

(65) Prior Publication Data
US 2022/0047820 A1     Feb. 17, 2022

(30) Foreign Application Priority Data
Sep. 27, 2018    (EP) ..................................... 18197289

(51) Int. Cl.
*A61M 11/00*     (2006.01)
*A61M 15/00*     (2006.01)
(Continued)

(52) U.S. Cl.
CPC ...... *A61M 11/006* (2014.02); *A61M 15/0036* (2014.02); *A61M 15/009* (2013.01);
(Continued)

(58) Field of Classification Search
CPC .. A61M 11/00; A61M 11/003; A61M 11/006; A61M 11/007; A61M 15/00;
(Continued)

(56) References Cited

U.S. PATENT DOCUMENTS 3,746,261 A    7/1973  Nozawa et al.
3,790,034 A *  2/1974  Horvath ................ B05B 9/0883
                                                        222/340
(Continued)

FOREIGN PATENT DOCUMENTS

CN    1315884 A    10/2001
CN    108495680 A    9/2018
(Continued)

OTHER PUBLICATIONS

International Search Report and Written Opinion for Int. App. No. PCT/EP2019/074313, mailed Nov. 26, 2019.

*Primary Examiner* — Colin W Stuart
(74) *Attorney, Agent, or Firm* — McDonnell Boehnen Hulbert & Berghoff LLP (57) ABSTRACT

A tensioning arrangement for an aerosol dispenser is presented where the tensioning arrangement has a conveying tube; an elastic member arranged to store mechanical energy from a substantially axial tensioning movement of the conveying tube; a rotatable member; a transmission mechanism configured to transmit a tensioning rotation of the rotatable member to the tensioning movement of the conveying tube, wherein the transmission mechanism has a cam profile and a cam follower arranged to follow the cam profile, wherein the cam profile has at least one priming structure; and wherein the tensioning arrangement is configured such that the conveying tube makes a temporary priming movement towards an initial position when the cam follower passes each priming structure during the tensioning movement of the conveying tube by means of the tensioning rotation of the rotatable member. An aerosol dispenser is also provided.

18 Claims, 7 Drawing Sheets

(51) Int. Cl.
    *G01F 11/00*         (2006.01)
    *G01F 11/02*         (2006.01)

(52) U.S. Cl.
    CPC .......... *G01F 11/006* (2013.01); *G01F 11/025* (2013.01); *A61M 11/007* (2014.02)

(58) Field of Classification Search
    CPC .......... A61M 15/0001; A61M 15/0013; A61M 15/0016; A61M 15/0028; A61M 15/0036; A61M 15/009
    See application file for complete search history.

(56) References Cited

U.S. PATENT DOCUMENTS

| | | | |
|---|---|---|---|
| 3,792,800 A * | 2/1974 | Capra | ................... B05B 9/0883 |
| | | | 222/340 |
| 5,964,416 A | 10/1999 | Jaeger et al. | |
| 6,945,472 B2 | 9/2005 | Wuttke et al. | |
| 2003/0042336 A1 | 3/2003 | Wuttke et al. | |
| 2003/0209238 A1 | 11/2003 | Peters et al. | |
| 2021/0252234 A1* | 8/2021 | Bartels | ................. A61M 11/007 |

FOREIGN PATENT DOCUMENTS

| | | |
|---|---|---|
| EP | 2044967 A1 | 4/2009 |
| JP | H11-512649 A | 11/1999 |
| KR | 10-0431011 B1 | 7/2004 |
| WO | 97/12687 A1 | 4/1997 |

\* cited by examiner

TENSIONING ARRANGEMENT FOR AEROSOL DISPENSER AND AEROSOL DISPENSER

CROSS REFERENCE TO RELATED APPLICATIONS

The present application is a U.S. National Phase Application pursuant to 35 U.S.C. § 371 of International Application No. PCT/EP2019/074313 filed Sep. 12, 2019, which claims priority to European Patent Application No. 18197289.4 filed Sep. 27, 2018. The entire disclosure contents of these applications are herewith incorporated by reference into the present application.

TECHNICAL FIELD

The present disclosure generally relates to a tensioning arrangement for an aerosol dispenser. In particular, a tensioning arrangement for an aerosol dispenser and an aerosol dispenser comprising the tensioning arrangement, are provided.

BACKGROUND

An aerosol dispenser is used to create an aerosol, i.e. a mist of liquid particles. Some aerosol dispensers use a gas to propel the liquid and some aerosol dispensers use mechanical solutions without a propelling gas to expel the liquid.

One type of aerosol dispenser comprises a base, a piston, a conveying tube, a spring, a dose chamber, a spray nozzle and a container, e.g. containing a drug. When the user rotates the base, e.g. 180°, the piston and the conveying tube are moved to compress the spring. As the conveying tube moves, the dose chamber is expanded and an underpressure is established therein. The underpressure causes the liquid in the container to be sucked into the dose chamber by the conveying tube. The user may then push a button to release the piston holding the conveying tube to expel a dose from the dose chamber through the spray nozzle as an aerosol.

U.S. Pat. No. 5,964,416 A discloses a miniaturized device for pressurizing fluid. The device includes a hollow piston that provides a fluid path and a valve member. The valve member is configured for axial movement so that the valve axis remains parallel to the piston axis. The valve member is arranged at one end of the hollow piston. The valve member may be partially or completely disposed within the hollow piston. The device is particularly adapted for use in a mechanically operated atomizer to produce an inhalable aerosol of a liquid medicament without the use of propellant gas.

SUMMARY

One problem with prior art aerosol dispensers, such as inhaler devices, is bacterial growth. In order to remove bacteria, a dedicated priming shot may be made with the aerosol dispenser such that bacteria is flushed out from various cavities. That is, the user may wind the base to fully tension the spring and make a priming shot into the air. For various reasons (unawareness of bacterial risks, carelessness etc.), users may however skip the priming shot. As a consequence, the problem with bacterial growth remains.

A further problem with prior art aerosol dispensers is when the liquid dries. When the aerosol dispenser has been inoperative for a while, e.g. a week, the performance might be deteriorated. For example, the expelled aerosol dose may be too small due to evaporation of the liquid, or it may be necessary to rinse residue from previous use of the aerosol dispenser. This problem may also be solved with the above-described dedicated priming shot. Again, however, the users often skip the priming shot.

Even if users make a priming shot each time before use of the aerosol dispenser, this is burdensome and time consuming for the user. At least for this reason, a still further problem with prior art aerosol dispensers is reduced usability.

A still further problem with prior art aerosol dispensers is that a priming shot may use too much liquid. Although some medical liquids used in aerosol dispensers are cheap, some are not.

A further problem with prior art aerosol dispensers is that if the patient loses grip of the base during wind-up, the power spring will unwind the mechanism to the beginning (i.e. to an initial position) and expel a dose into the air.

A still further problem with prior art aerosol dispensers is that the user has to continuously turn the base over a relatively large angular distance, e.g. 180°, until the tensioning arrangement is set in a tensioned position.

A still further problem with prior art dispensers is that the user has to turn the base with relatively high force in order to set the tensioning arrangement in a tensioned position.

One object of the present disclosure is to provide an arrangement for an aerosol dispenser, which arrangement contributes to an improved hygiene of the aerosol dispenser.

A further object of the present disclosure is to provide an arrangement for an aerosol dispenser, which arrangement contributes to an improved performance of the aerosol dispenser.

A still further object of the present disclosure is to provide a tensioning arrangement for an aerosol dispenser, which tensioning arrangement improves usability of the aerosol dispenser.

A still further object of the present disclosure is to provide a tensioning arrangement for an aerosol dispenser, which tensioning arrangement solves several or all of the foregoing objects in combination.

A still further object of the present disclosure is to provide an aerosol dispenser solving one, several or all of the foregoing objects.

According to one aspect, there is provided a tensioning arrangement for an aerosol dispenser, the tensioning arrangement comprising a conveying tube for conveying liquid from a container to a dose chamber; an elastic member arranged to store mechanical energy from a substantially axial, or axial, tensioning movement of the conveying tube from an initial position to a tensioning position; a rotatable member; a transmission mechanism configured to transmit a tensioning rotation of the rotatable member to the tensioning movement of the conveying tube; wherein the transmission mechanism comprises a cam profile and a cam follower arranged to follow the cam profile; wherein the cam profile comprises at least one priming structure; and wherein the tensioning arrangement is configured such that the conveying tube makes a temporary priming movement towards the initial position when the cam follower passes each priming structure during the tensioning movement of the conveying tube by means of the tensioning rotation of the rotatable member.

As the conveying tube makes the tensioning movement, an underpressure is created in the dose chamber. This underpressure causes liquid to be sucked from the container and delivered to the dose chamber by means of the conveying tube. In addition, when the cam follower travels over the at least one priming structure on the cam profile, the conveying tube makes an additional small backward or distal movement and an additional small forward or proximal movement. The small proximal movement is in a releasing direction opposite to a tensioning direction of the tensioning movement. The small forward movement of the conveying tube causes a small dose of liquid to be expelled that fills out dry cavities in the aerosol dispenser (e.g. in a spray nozzle unit of the aerosol dispenser) and pushes out foreign particles, such as bacteria or residue.

Thereby, due to the at least one priming movement made by the conveying tube when the rotatable member is rotated, at least one priming function is carried out when the conveying tube is in liquid communication with the container. The tensioning arrangement according to the present disclosure may therefore be referred to as a priming mechanism. Thus, every time a tensioning operation is made (i.e. rotation of the rotatable member such that the conveying tube is moved from the initial position to the tensioning position), at least one priming function is carried out. Thereby, dedicated priming shots can be avoided.

Throughout the present disclosure, the tensioning arrangement may alternatively be referred to as a wind-up mechanism. The at least one priming structure may be integrated with the cam profile, e.g. a protruding priming structure may be integrally formed with the cam profile and a recessed priming structure may be formed by a cut-out in the cam profile.

Throughout the present disclosure, the rotatable member may be constituted by a rotatable base of an aerosol dispenser. The tensioning arrangement according to the present disclosure may comprise one or several pairs of a cam profile and a cam follower associated with the cam profile. Alternatively, the tensioning arrangement may comprise only one cam profile and several cam followers for following the cam profile. As a further alternative, the tensioning arrangement may comprise several cam profiles and only one cam follower for following the cam profiles. The at least one cam profile may be constituted by one or more slopes.

One of the at least one priming structure may be positioned less than 20%, such as less than 10%, such as less than 5%, of a cam profile length along the cam profile from a position corresponding to the initial position. Alternatively, or in addition, the at least one priming structure may be constituted by a plurality of priming structures substantially evenly distributed over a cam profile length along the cam profile from a position corresponding to the initial position to a position corresponding to the tensioning position. In this case, the tensioning arrangement can expel a plurality of small priming doses during a single tensioning rotation of the rotatable member.

The at least one priming structure may be arranged to prevent the rotatable member from rotating in a direction opposite to the tensioning rotation. In other words, unwinding of the rotatable member, i.e. rotation of the rotatable member in a direction opposite to the tensioning rotation, is prevented, for example if the user loses grip of the rotatable member. The user can thereby tension the tensioning arrangement intermittently, i.e. with a plurality of sequential tensioning rotations of the rotatable member. This is for example helpful for elderly and/or weak users.

When the at least one priming structure is arranged to prevent the rotatable member from rotating in a direction opposite to the tensioning rotation, the tensioning arrangement may be referred to as a priming and unwinding preventing mechanism or as a priming wind-up mechanism that prevents unwinding. Thus, the at least one priming structure according to the present disclosure may generate two functions in combination, namely the priming function and the unwinding preventing function.

Furthermore, the variant where the at least one priming structure is arranged to prevent the rotatable member from rotating in a direction opposite to the tensioning rotation may be constituted by a ratchet mechanism. In this case, the at least one priming structure may constitute one or more teeth of the ratchet mechanism, and the cam follower may constitute a pawl of the ratchet mechanism. Thus, the present disclosure provides a ratchet mechanism integrated in the transmission mechanism of the tensioning arrangement.

The tensioning arrangement may further comprise a movable holding member holding the conveying tube, and the cam follower may be fixed in relation to the holding member. Throughout the present disclosure, the holding member may be referred to as a piston.

The cam follower may be integral with the holding member. The cam follower and the holding member may for example be injection moulded.

The cam profile may be a helical surface. The helical surface may for example extend 140° to 175° around a longitudinal axis of the aerosol dispenser.

Each of the at least one priming structure may be constituted by a protrusion. Each priming structure may protrude 0.1-0.8 mm, such as 0.2-0.6 mm, such as approximately 0.4 mm from an adjacent surface of the cam profile.

Each of the at least one priming structure may be wedge-shaped. Alternatively, each of the at least one priming structure may be constituted by a protruding knob. In case the cam profile comprises a plurality of priming structures, the priming structures may be different, including for example a combination of wedges and knobs.

The at least one priming structure may comprise a priming structure surface at an angle of 5° to 30°, such as 5° to 15°, to an adjacent surface of the cam profile. The at least one priming structure may extend partially or fully over a width of the cam profile, e.g. in a lateral direction of the aerosol dispenser.

Each of the at least one priming structure may be constituted by a recess. In this case, each recess may have a depth of 0.1-0.8 mm, such as 0.2-0.6 mm, such as approximately 0.4 mm from an adjacent surface of the cam profile.

The tensioning arrangement according to the present disclosure may further comprise a stationary part. In this case, the cam profile may be provided on the stationary part.

The cam profile may be integral with the stationary part. The cam profile may for example be provided on a distal end of the stationary part facing the rotatable member.

A sum of a distance of each priming movement of the conveying tube may be 10-50%, such as 15-35%, such as 15-25%, such as approximately 20%, of a tensioning distance of the conveying tube from the initial position to the tensioning position. The tensioning distance may for example be 8-10 mm. Throughout the present disclosure, the sum of the distance of each priming movement may be referred to as a total priming distance.

According to a further aspect, there is provided an aerosol dispenser comprising a tensioning arrangement according to the present disclosure. The aerosol dispenser may for example be constituted by an inhaler device.

The aerosol dispenser may comprise a dose chamber. The volume of the dose chamber may be defined by the position of the conveying tube. The volume of the dose chamber may be expanded when the conveying tube makes the tensioning movement and may be compressed when the conveying tube makes the priming movement.

BRIEF DESCRIPTION OF THE DRAWINGS

Further details, advantages and aspects of the present disclosure will become apparent from the following embodiments taken in conjunction with the drawings, wherein.

DETAILED DESCRIPTION

In the following, a tensioning arrangement for an aerosol dispenser and an aerosol dispenser comprising the tensioning arrangement, will be described. The same reference numerals will be used to denote the same or similar structural features.

Figure 1:
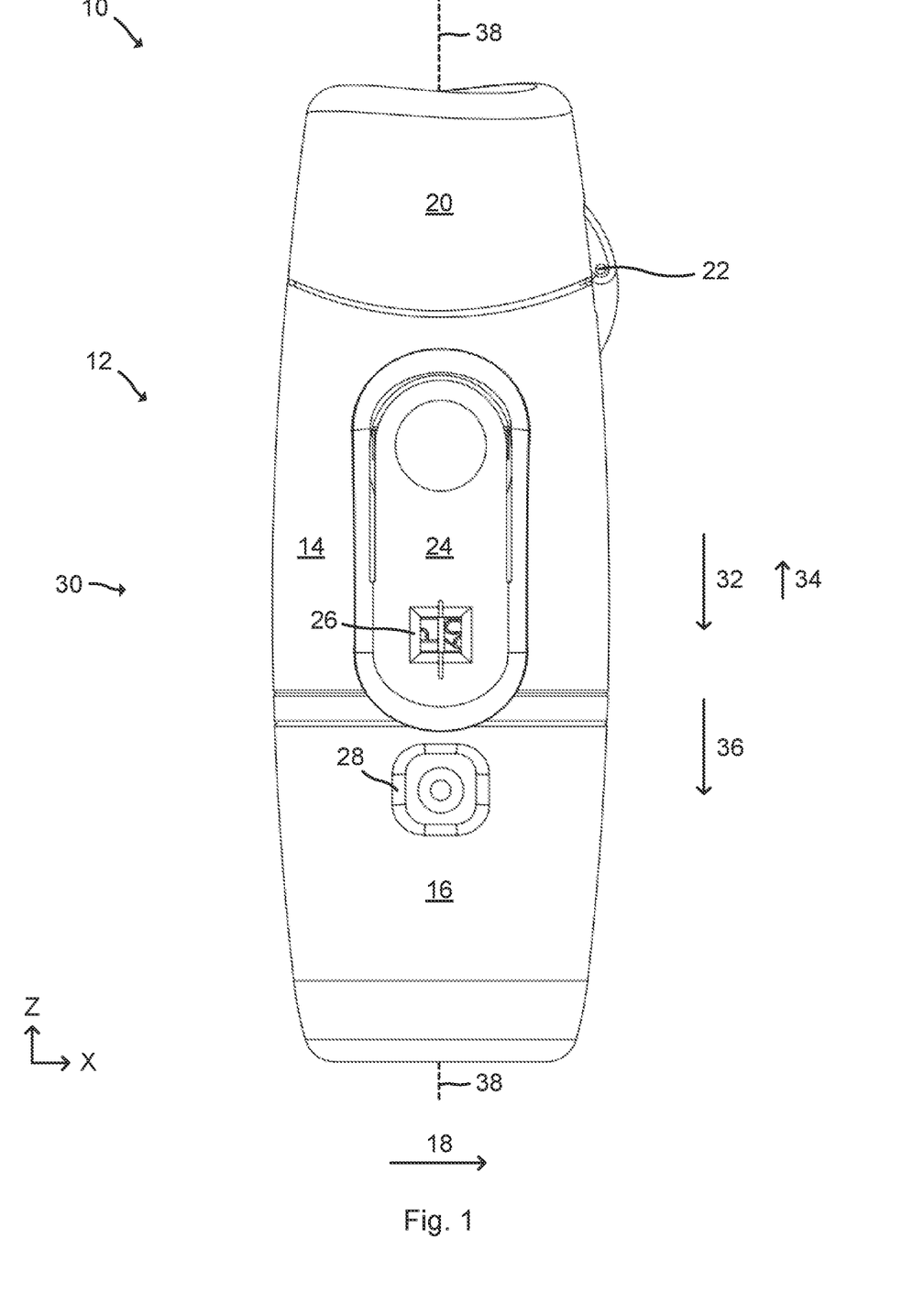
FIG. 1 represents a side view of an aerosol dispenser comprising a tensioning arrangement.

FIG. 1 represents a side view of one example of an aerosol dispenser 10 comprising a tensioning arrangement 12. The aerosol dispenser 10 comprises a housing 14 and a rotatable member 16 rotatable relative to the housing 14 to make a tensioning rotation 18. In FIG. 1, the rotatable member 16 is constituted by an outer base of the aerosol dispenser 10. However, the rotatable member 16 may alternatively be constituted by, for example, an intermediate exterior portion of the aerosol dispenser 10.

The aerosol dispenser 10 in FIG. 1 further comprises an openable lid 20, connected to the housing 14 via a hinge 22, and a button 24 for triggering a dose shot. The aerosol dispenser 10 of this example further comprises a dose indicator 26 that indicates the number of doses left in the aerosol dispenser 10 and a state indicator 28 that indicates a loading state of the aerosol dispenser 10 (e.g. unloaded or loaded with a container).

In FIG. 1, a needle or conveying tube (not shown) within the aerosol dispenser 10 is in an initial position 30. FIG. 1 further denotes an axial tensioning movement 32 and an axial priming movement 34 for the conveying tube. The tensioning movement 32 is made in a tensioning direction 36 along a longitudinal axis 38 of the aerosol dispenser 10. The tensioning direction 36 may be said to be in a distal direction, i.e. towards the rotatable member 16. FIG. 1 further shows a Cartesian coordinate system for referencing purposes. The aerosol dispenser 10 may however be oriented arbitrarily in space.

Figure 2:
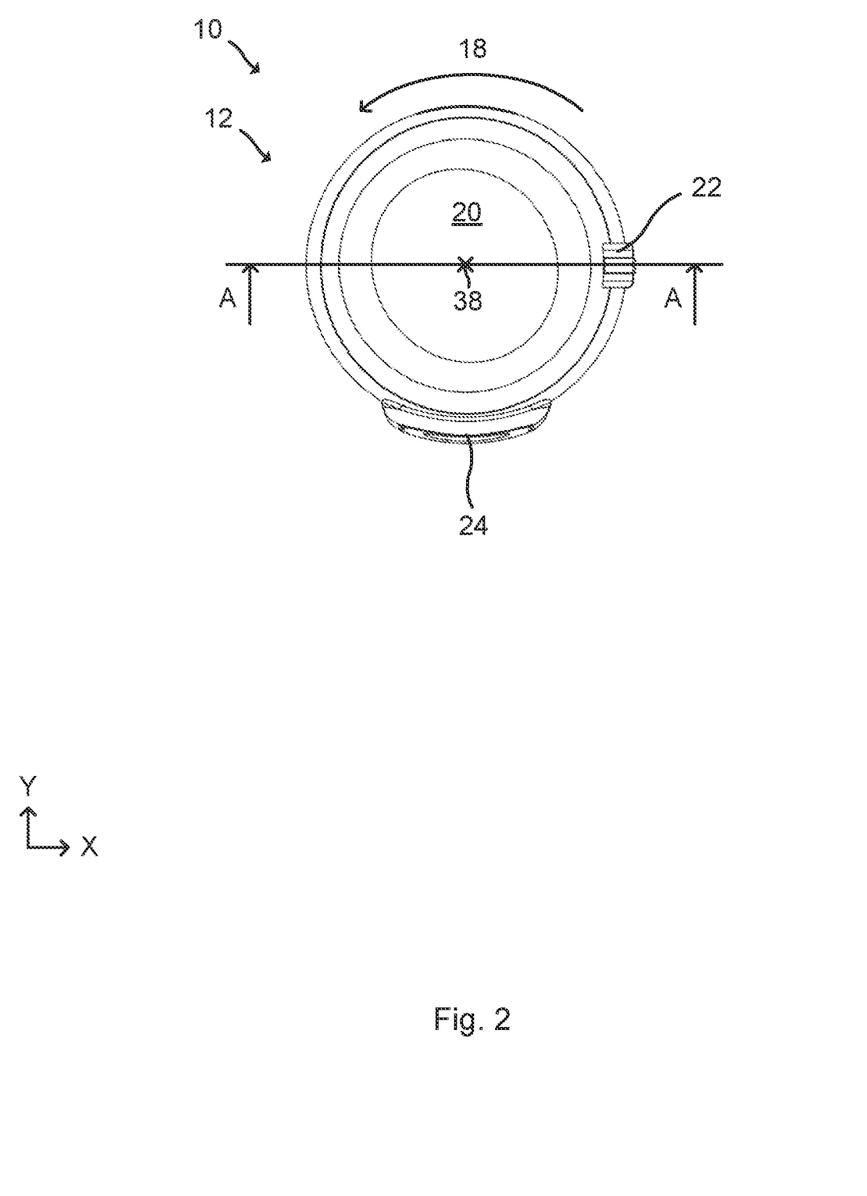
FIG. 2 represents a top view of the aerosol dispenser.

FIG. 2 represents a top view of the aerosol dispenser 10. As can be seen in FIGS. 1 and 2, the aerosol dispenser 10 of this example has a generally cylindrical shape.

Figure 3:
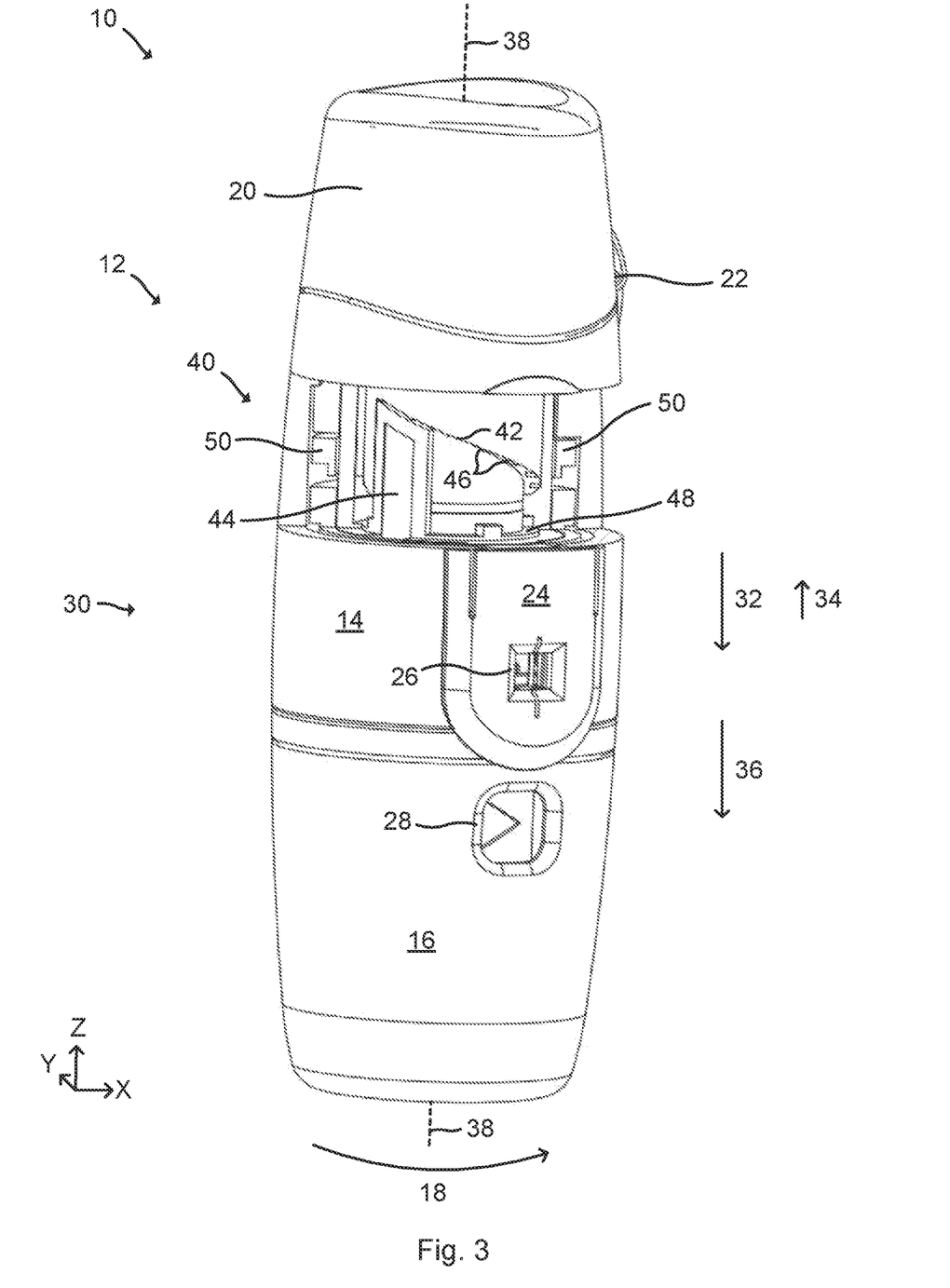
FIG. 3 represents a perspective partially cut-out view of the aerosol dispenser.

FIG. 3 represents a perspective partially cut-out view of the aerosol dispenser 10. In the cut-out section of FIG. 3, it can be seen that the tensioning arrangement 12 comprises a transmission mechanism 40. The transmission mechanism 40 is configured to transmit the tensioning rotation 18 of the rotatable member 16 to the tensioning movement 32 of the conveying tube (not shown) along the longitudinal axis 38 of the aerosol dispenser 10.

The tensioning arrangement 12 of this example comprises two cam profiles 42 (only one is visible in FIG. 3) and two cam followers 44 (only one is visible in FIG. 3), each arranged to follow a respective cam profile 42. Each cam profile 42 of this example is a helical surface concentric with the longitudinal axis 38 of the aerosol dispenser 10. The tensioning arrangement 12 may alternatively comprise only one pair of a cam profile 42 and a cam follower 44, or more than two pairs. As a further alternative, the tensioning arrangement 12 may comprise only one cam profile 42 and two or more cam followers 44. As a further alternative, the tensioning arrangement 12 may comprise two or more cam profiles 42 and only one cam follower 44.

A plurality of priming structures 46 are provided on each cam profile 42. Each priming structure 46 is arranged to prevent the rotatable member 16 from rotating in a direction opposite to the tensioning rotation 18. This is useful if for example the patient loses the grip of the rotatable member 16 when making the tensioning rotation 18. In the example of FIG. 3, each priming structure 46 is constituted by a protrusion.

In the cut-out section of FIG. 3, a piston or holding member 48 of the tensioning arrangement 12 can also be seen. The holding member 48 holds the conveying tube (not shown). In the example in FIG. 3, the two cam followers 44 are fixed relative to the holding member 48. More specifically, each cam follower 44 is integrally formed with the holding member 48 and projects in parallel with the longitudinal axis 38 towards the cam profile 42, i.e. in a proximal direction.

Furthermore, in the cut-out section of FIG. 3, an actuator member 50 of the aerosol dispenser 10, here implemented as an actuator ring, can be seen. The actuator member 50 is movable between a blocking position, in which the actuator member 50 blocks the holding member 48 and the conveying tube 52 from being released, and an unblocking position. In FIG. 3, the actuator member 50 is in the unblocking position. The actuator member 50 can be moved from the unblocking position to the blocking position by means of the tensioning rotation 18 of the rotatable member 16. The button 24 is operatively coupled to the actuator member 50. By pushing the button 24, the actuator member 50 can be moved from the blocking position to the unblocking position, i.e. the actuator member 50 can be released to expel an aerosol.

Figure 4:
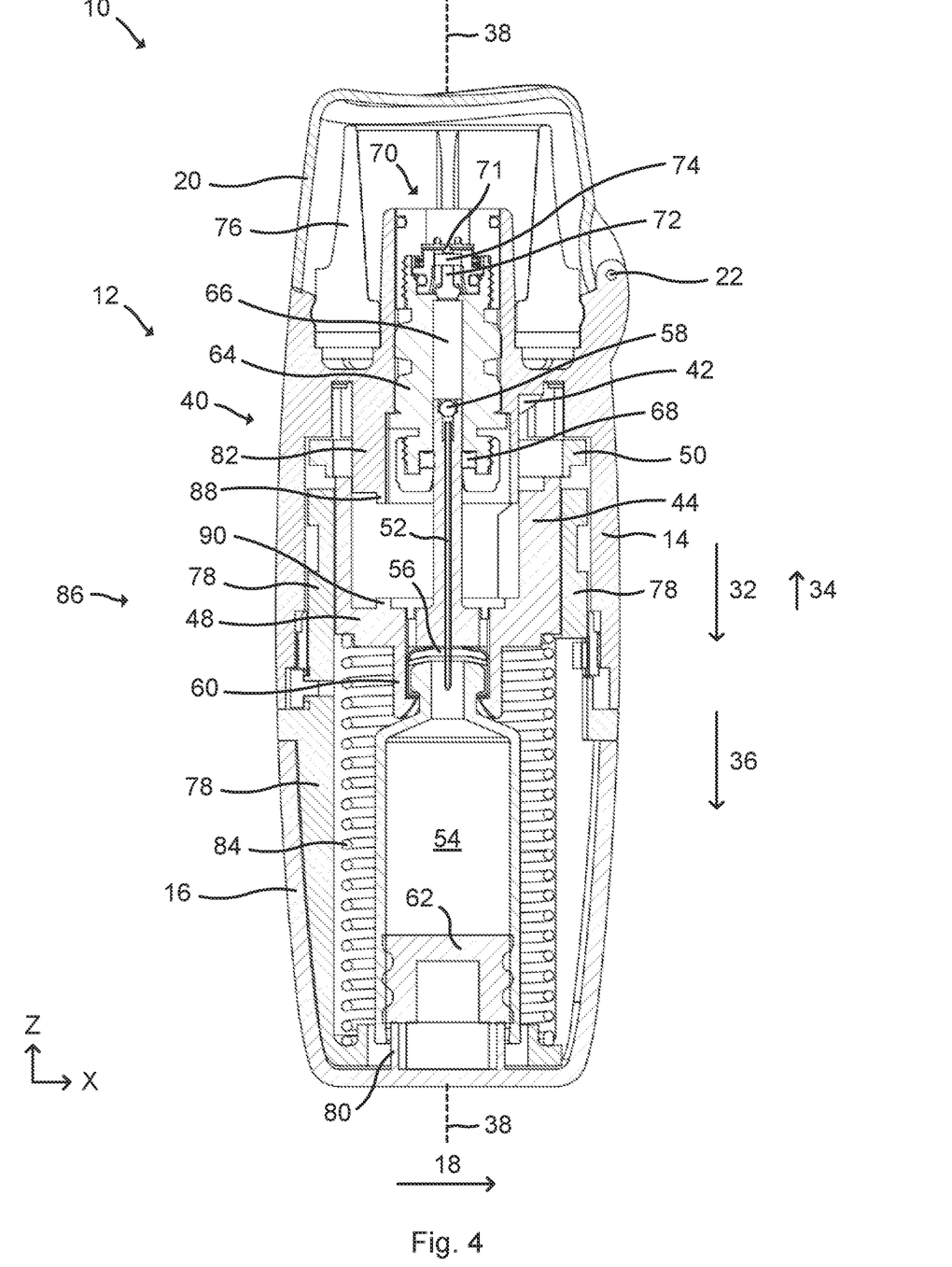
FIG. 4 represents a cross-sectional view of the aerosol dispenser along line A-A in FIG. 2.
Figure 5:
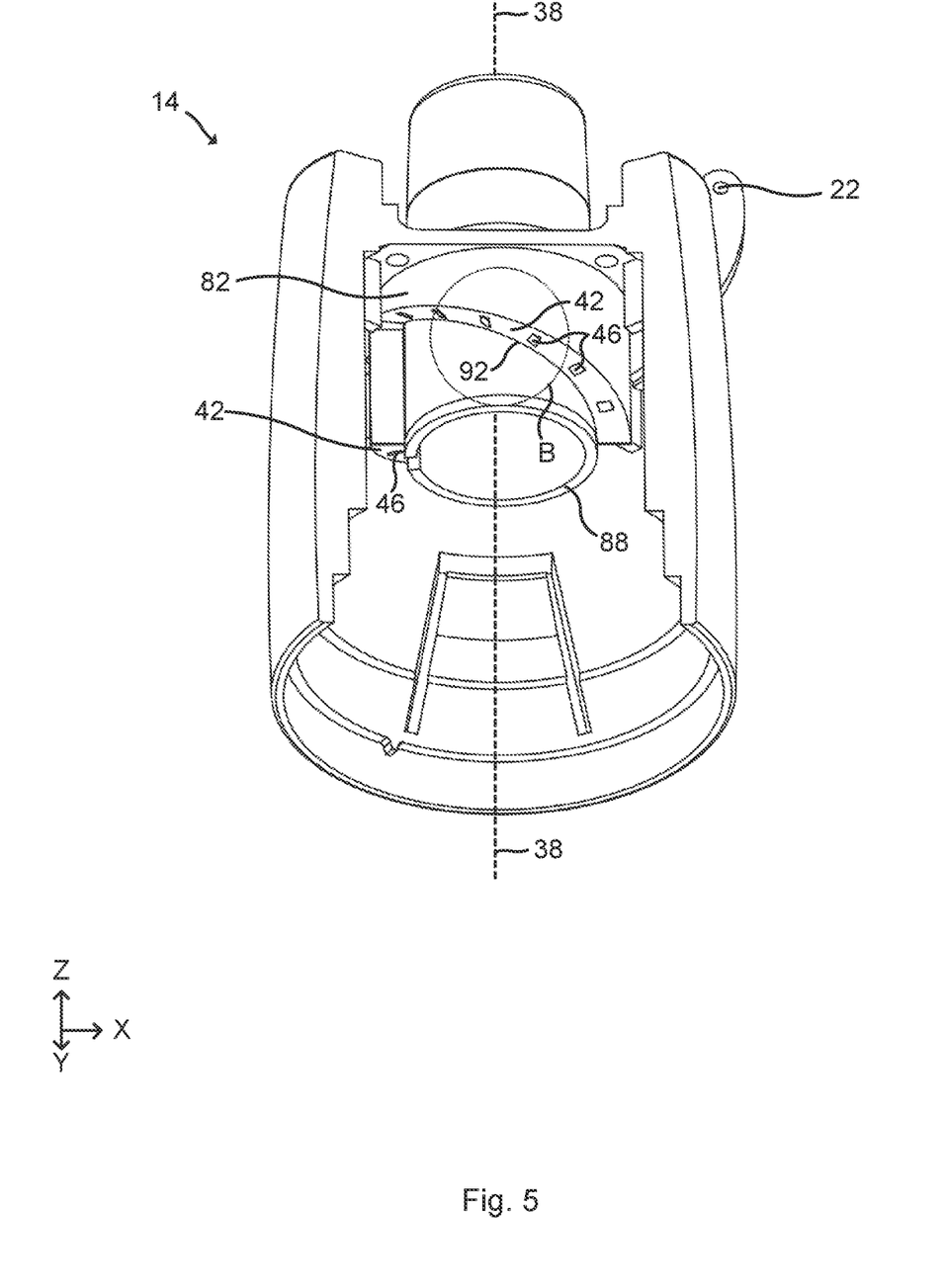
FIG. 5 represents a partial perspective view of a housing of the aerosol dispenser.
Figure 6:
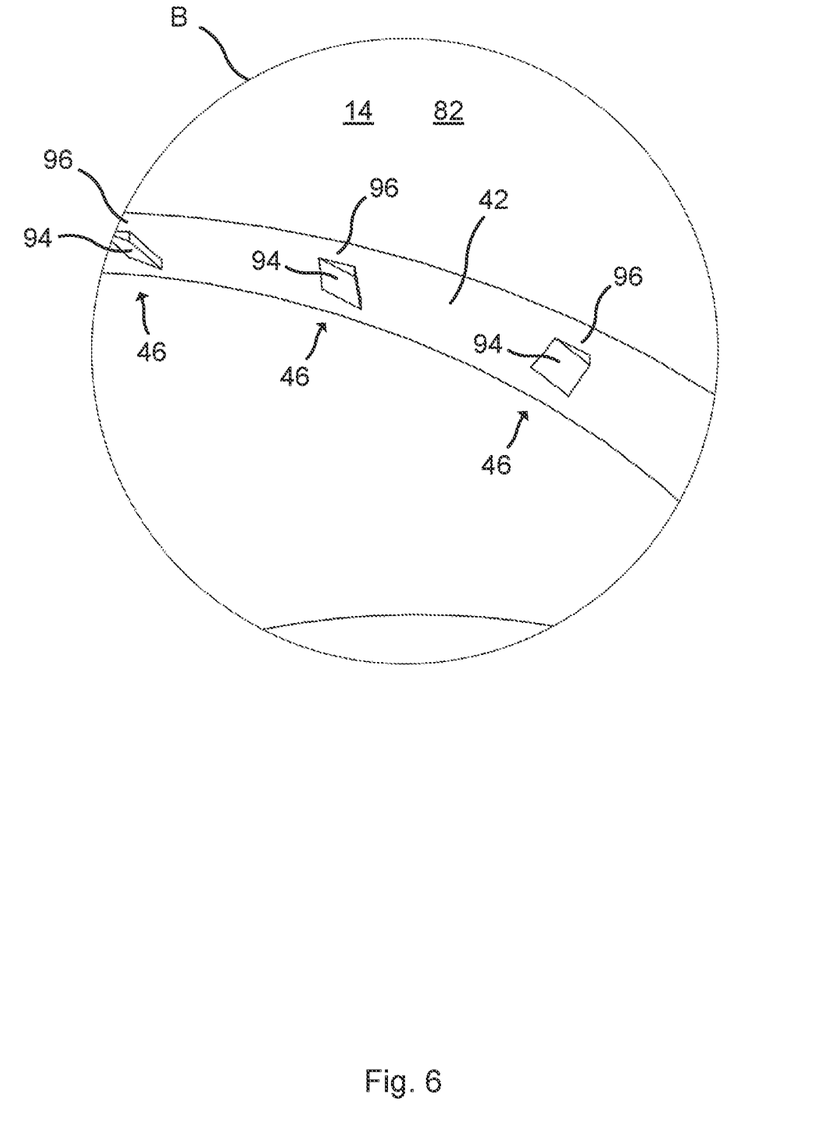
FIG. 6 represents an enlarged view of section B in FIG. 5.

FIG. 4 represents a cross-sectional view of the aerosol dispenser 10 along line A-A in FIG. 2. In FIG. 4, the conveying tube 52 of the tensioning arrangement 12 can be seen. The aerosol dispenser 10 is loaded with a container 54 containing liquid, such as a drug, to be dispensed as an aerosol.

The conveying tube 52 has pierced a closure 56 of the container 54 and is thereby brought into communication with the liquid in the container 54. The conveying tube 52 comprises an optional conveying tube check valve 58 at a proximal end of the conveying tube 52, i.e. at an opposite end with respect to the container 54. In this example, the neck of the container 54 is held by a locking structure 60 on the holding member 48. The locking structure 60 is here exemplified as a plurality of resilient arms projecting from the holding member 48 towards the rotatable member 16. The container 54 comprises a stopper 62 that closes the bottom of the container 54.

The aerosol dispenser 10 of this example comprises a stationary pump cylinder 64, i.e. stationary with respect to the housing 14. A dose chamber 66 is provided in the pump cylinder 64. The conveying tube 52 is movable back and forth to expand and compress the volume of the dose chamber 66. A sealing 68, here exemplified as an X-ring, is provided to seal between the conveying tube 52 and the pump cylinder 64. The sealing 68 may alternatively be constituted by an O-ring, or other types of sealings known in the art.

The aerosol dispenser 10 further comprises a spray nozzle unit 70 having a spray nozzle 71 at a proximal side of the dose chamber 66. The spray nozzle unit 70 may for example comprise a spray nozzle check valve 72 and a membrane or filter 74. The aerosol dispenser 10 further comprises a mouthpiece 76 which is exposed to a user by opening the lid 20.

As can be seen in FIG. 4, the transmission mechanism 40 of this example also comprises an inner sleeve 78. The inner sleeve 78 is fixedly connected to the rotatable member 16. The inner sleeve 78 and the holding member 48 are rotationally coupled. However, the holding member 48 is allowed to move axially relative to the inner sleeve 78 and the rotatable member 16. This type of coupling between the inner sleeve 78 and the holding member 48 may for example be realized by means of a pin or rib engaged in a slot parallel with the longitudinal axis 38. The rotatable member 16 of this example comprises a proximally protruding collar 80 for contacting the stopper 62 of the container 54.

In the example in FIG. 4, the cam profiles 42 are provided on a stationary part 82, here constituted by a central part of the housing 14. The cam profiles 42 are integrally formed with the stationary part 82 and faces in the distal direction, i.e. towards the rotatable member 16.

The arrangement of the cam profiles 42 and the cam followers 44 may alternatively be reversed. That is, the cam profiles 42 may be provided on the holding member 48 and the cam followers 44 may be provided on the stationary part 82.

The tensioning arrangement 12 further comprises an elastic member 84, here constituted by a compression coil spring enclosing the container 54. The elastic member 84 is arranged to store mechanical energy from the tensioning movement 32 of the holding member 48 and the conveying tube 52 from the initial position 30 in FIG. 3 to a tensioning position 86 according to FIG. 4.

FIG. 4 further shows a housing stop 88 projecting distally from the housing 14 and a holding member stop 90 projecting proximally from the holding member 48. Expansion of the elastic member 84 is limited when the holding member stop 90 contacts the housing stop 88.

When the rotatable member 16 is manually rotated, the optional inner sleeve 78 rotates together with the rotatable member 16. The tensioning rotation 18 of the rotatable member 16 and the inner sleeve 78 is transmitted to a rotation of the holding member 48. The rotation of the holding member 48 causes the cam followers 44 to travel along the associated cam profiles 42. Due to the cooperation between the cam followers 44 and the cam profiles 42, the tensioning rotation 18 of the rotatable member 16 is transmitted to the tensioning movement 32 of the conveying tube 52 and the holding member 48 in the distal tensioning direction 36 against the force of the elastic member 84 until the conveying tube 52 has moved from the initial position 30 to the tensioning position 86 according to FIG. 4.

In FIG. 4, the actuator member 50 is in the blocking position and holds the holding member 48 and the conveying tube 52 in the tensioning position 86. In this state, the tensioning arrangement 12 is tensioned. In the blocking position of the actuator member 50, the force from the elastic member 84 pushes the holding member 48 and the actuator member 50 against the housing 14. The actuator member 50 is thereby clamped between the holding member 48 and the housing 14.

As the conveying tube 52 moves in the tensioning direction 36, the volume of the dose chamber 66 expands and an underpressure is established in the dose chamber 66.

Consequently, liquid in the container 54 is sucked by the conveying tube 52 into the dose chamber 66. The holding member 48 and the conveying tube 52 is then held in the tensioning position 86 by means of the actuator member 50. When the conveying tube 52 is in the tensioning position 86, the volume of the dose chamber 66 corresponds to one dose.

When the user pushes the button 24, the actuator member 50 is moved to its unblocking position such that the actuator member 50 no longer blocks the holding member 48. As a consequence, the entire force from the elastic member 84 acts on the liquid in the dose chamber 66 via the holding member 48, the conveying tube 52 and the conveying tube check valve 58. The force in the elastic member 84 may for example be 5-50 N. The high pressure in the dose chamber 66 presses the liquid through the spray nozzle check valve 72 and the filter 74 of the spray nozzle unit 70. The liquid is thereby expelled as an aerosol. The pressure in the dose chamber 66 may be approximately 15-75 bar. In view of prior art, this enables the use of a relatively weak spring as elastic member 84.

FIG. 5 represents a partial perspective view of a housing 14 of the aerosol dispenser 10. In FIG. 5, it can be seen that the cam profile 42 comprises a cam profile length 92. The cam profile length 92 of this example extends over an angular distance of approximately 150° around the longitudinal axis 38.

The leftmost proximal position on the front cam profile 42 corresponds to the initial position 30 of the conveying tube 52. The rightmost distal position on the front cam profile 42 corresponds to the tensioning position 86 of the conveying tube 52.

The priming structures 46 are evenly distributed over the cam profile length 92 from the position corresponding to the initial position 30 (in this example the leftmost proximal position) to the position corresponding to the tensioning position 86 (in this example the rightmost distal position). In FIG. 5, the cam profile 42 comprises six priming structures 46. The first priming structure 46, i.e. the leftmost priming structure 46 of the front cam profile 42 in FIG. 5, is positioned less than 20% (approximately 14%) of the cam profile length 92 from the position corresponding to the initial position 30 of the conveying tube 52 (in this example the leftmost proximal position). The above also applies for the rear cam profile 42 which is not fully visible in FIG. 5.

FIG. 6 represents an enlarged view of section B in FIG. 5. In FIG. 6, it can be seen that each priming structure 46 is wedge-shaped. More specifically, each priming structure 46 comprises a priming structure surface 94 at an angle of approximately 10° to its adjacent surface 96 of the cam profile 42.

When the rotatable member 16 is manually rotated to make the tensioning rotation 18 and the cam followers 44 travel along the associated cam profiles 42, the conveying tube 52 generally makes the tensioning movement 32 in the tensioning direction 36 from the initial position 30 to the tensioning position 86. However, when the cam followers 44 travel over a priming structure 46 on an associated cam profile 42, the conveying tube 52 makes a temporary priming movement 34 towards the initial position 30, i.e. in the proximal direction of the aerosol dispenser 10. Each priming movement 34 is shorter than the tensioning movement 32.

When the conveying tube 52 makes a priming movement 34, the dose chamber 66 is compressed and a small volume of liquid (corresponding to the length of the priming movement 34) is expelled that fills out dry cavities in the aerosol dispenser 10 (e.g. in the spray nozzle unit 70) and pushes out foreign particles, such as bacteria and/or residue, from the spray nozzle unit 70. The small volumes of liquid may be referred to as priming doses.

Figure 7:
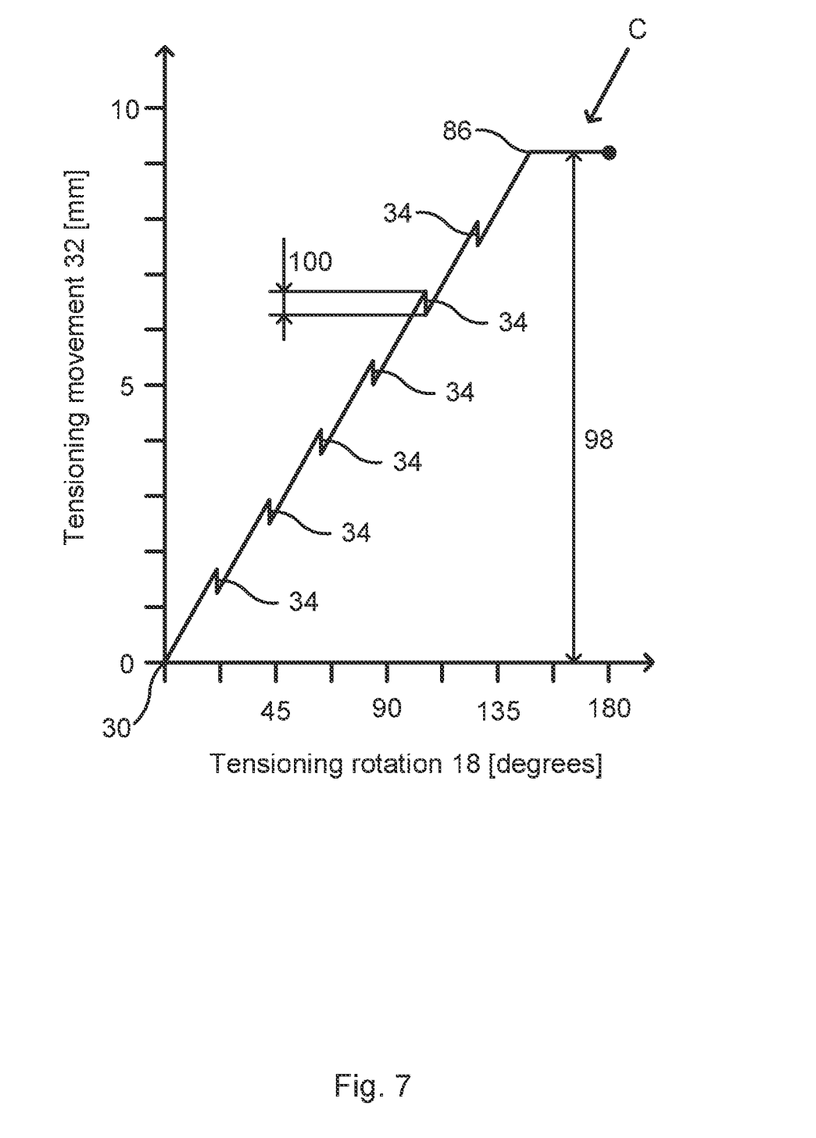
FIG. 7 shows a diagram of an example movement of a conveying tube of the aerosol dispenser.

FIG. 7 shows a diagram of an example movement of the conveying tube 52 of the aerosol dispenser 10. More specifically, FIG. 7 shows the tensioning movement 32 and the priming movements 34 of the conveying tube 52 as a function of the tensioning rotation 18 of the rotatable member 16.

FIG. 7 further shows a tensioning distance 98, which is the axial length of the tensioning movement 32 of the conveying tube 52. In FIG. 7, the tensioning distance 98 is approximately 9.2 mm.

FIG. 7 further shows a priming distance 100 for one of the priming movements 34. The priming distance 100 may be the same for all priming movements 34, or different. In FIG. 7, all priming distances 100 have the same length of approximately 0.4 mm. A sum of a distance of all priming movements 34 of the conveying tube 52 is approximately 24% of the tensioning distance 98.

The horizontal line C in FIG. 7 indicates the most tensioned position of the conveying tube 52. During the last tensioning rotation 18 of the rotatable member 16, e.g. from approximately 150° to 180°, the actuator member 50 is pushed laterally from the unblocking position to the blocking position to thereby block the holding member 48.

While the present disclosure has been described with reference to exemplary embodiments, it will be appreciated that the present disclosure is not limited to what has been described above. For example, it will be appreciated that the dimensions of the parts may be varied as needed.

The invention claimed is:

1. A tensioning arrangement for an aerosol dispenser, the tensioning arrangement comprising:
- a conveying tube for conveying liquid from a container to a dose chamber;
- an elastic member arranged to store mechanical energy from an axial tensioning movement of the conveying tube from an initial position to a tensioning position;
- a rotatable member;
- a transmission mechanism configured to transmit a tensioning rotation of the rotatable member to the tensioning movement of the conveying tube;
- wherein the transmission mechanism comprises a cam profile and a cam follower arranged to follow the cam profile;
- wherein the cam profile comprises at least one priming structure;
- wherein each of the at least one priming structure is constituted by a protrusion; and
- wherein the tensioning arrangement is configured such that the conveying tube makes a temporary priming movement towards the initial position when the cam follower passes each priming structure during the tensioning movement of the conveying tube by means of the tensioning rotation of the rotatable member.

2. The tensioning arrangement according to claim 1, wherein one of the at least one priming structure is positioned less than 20% of a cam profile length along the cam profile from a position corresponding to the initial position.

3. The tensioning arrangement according to claim 1, wherein the at least one priming structure is constituted by a plurality of priming structures evenly distributed over a cam profile length along the cam profile from a position corresponding to the initial position to a position corresponding to the tensioning position.

4. The tensioning arrangement according to claim 1, wherein the at least one priming structure is arranged to prevent the rotatable member from rotating in a direction opposite to the tensioning rotation.

5. The tensioning arrangement according to claim 1, further comprising a movable holding member holding the conveying tube, and wherein the cam follower is fixed in relation to the holding member.

6. The tensioning arrangement according to claim 5, wherein the cam follower is integral with the holding member.

7. The tensioning arrangement according to claim 1, wherein the cam profile is a helical surface.

8. The tensioning arrangement according to claim 1, wherein each of the at least one priming structure is wedge-shaped.

9. The tensioning arrangement according to claim 8, wherein the at least one priming structure comprises a priming structure surface at an angle of 5° to 30° to an adjacent surface of the cam profile.

10. The tensioning arrangement according to claim 1, further comprising a stationary part, and wherein the cam profile is provided on the stationary part.

11. The tensioning arrangement according to claim 10, wherein the cam profile is integral with the stationary part.

12. The tensioning arrangement according to claim 1, wherein a sum of a distance of each priming movement of the conveying tube is 10-50% of a tensioning distance of the conveying tube from the initial position to the tensioning position.

13. An aerosol dispenser comprising the tensioning arrangement according to claim 1.

14. A tensioning arrangement for an aerosol dispenser, the tensioning arrangement comprising:
- a conveying tube for conveying liquid from a container to a dose chamber;
- an elastic member arranged to store mechanical energy from an axial tensioning movement of the conveying tube from an initial position to a tensioning position;
- a movable holding member that holds the conveying tube
- a rotatable member;
- a transmission mechanism configured to transmit a tensioning rotation of the rotatable member to the tensioning movement of the conveying tube;
- wherein the transmission mechanism comprises a cam profile and a cam follower arranged to follow the cam profile;
- wherein the cam profile comprises a plurality of priming structures; and
- wherein the tensioning arrangement is configured such that the conveying tube makes a temporary priming movement towards the initial position when the cam follower passes each priming structure during the tensioning movement of the conveying tube by means of the tensioning rotation of the rotatable member.

15. The tensioning arrangement of claim 14, wherein the plurality of priming structures are evenly distributed over a cam profile length along the cam profile from a position corresponding to the initial position to a position corresponding to the tensioning position.

16. The tensioning arrangement of claim 14, wherein the cam follower is fixed in relation to the holding member.

17. The tensioning arrangement of claim 14, wherein the cam profile is a helical surface.

18. The tensioning arrangement of claim 14, wherein each of the plurality of priming structures is wedge-shaped.

\* \* \* \* \*